United States Patent
Maciá Barber et al.

(10) Patent No.: US 11,497,450 B2
(45) Date of Patent: *Nov. 15, 2022

(54) SYSTEM AND METHODS FOR ADAPTIVE NOISE QUANTIFICATION IN DYNAMIC BIOSIGNAL ANALYSIS

(71) Applicant: Smart Solutions Technologies, S.L., Madrid (ES)

(72) Inventors: Agustín Maciá Barber, Madrid (ES); Xavier Ibáñez Català, Valencia (ES)

(73) Assignee: Smart Solutions Technologies, S.L., Madrid (ES)

( * ) Notice: Subject to any disclaimer, the term of this patent is extended or adjusted under 35 U.S.C. 154(b) by 367 days.

This patent is subject to a terminal disclaimer.

(21) Appl. No.: 16/781,402

(22) Filed: Feb. 4, 2020

(65) Prior Publication Data

US 2020/0170577 A1    Jun. 4, 2020

Related U.S. Application Data

(63) Continuation of application No. 15/209,506, filed on Jul. 13, 2016.

(Continued)

(30) Foreign Application Priority Data

Jul. 14, 2015    (ES) .................................. 201531026

(51) Int. Cl.
*A61B 5/00* (2006.01)
*A61B 5/282* (2021.01)
*A61B 5/318* (2021.01)

(52) U.S. Cl.
CPC .............. *A61B 5/721* (2013.01); *A61B 5/282* (2021.01); *A61B 5/318* (2021.01); *A61B 5/6804* (2013.01);

(Continued)

(58) Field of Classification Search
CPC ......... A61B 5/721; A61B 5/282; A61B 5/318; A61B 5/6804; A61B 5/6805;

(Continued)

(56) References Cited

U.S. PATENT DOCUMENTS

2007/0173734 A1    7/2007    Kim et al.
2009/0062696 A1    3/2009    Nathan et al.
(Continued)

FOREIGN PATENT DOCUMENTS

JP    2011156376 A    8/2011
WO    2014145618 A1    9/2014

OTHER PUBLICATIONS

International Search Report and Written Opinion, PCT/EP2016/066802, dated Nov. 28, 2016.

*Primary Examiner* — Sean P Dougherty
(74) *Attorney, Agent, or Firm* — Entralta; Peter D. Weinstein; James F. Fleming

(57) ABSTRACT

An adaptive noise quantification system and associated methods are disclosed for use in the dynamic biosignal analysis of a user. In at least one embodiment, the system includes a biosignal sensor positioned and configured for obtaining and transmitting data related to a select at least one vital of the user as a biosignal, and a motion sensor positioned and configured for obtaining and transmitting data related to a motion level of the user as a motion signal. A computing device is configured for receiving and processing the biosignal and motion signal.

14 Claims, 3 Drawing Sheets

Related U.S. Application Data

(60) Provisional application No. 62/192,504, filed on Jul. 14, 2015.

(52) U.S. Cl.
CPC .......... *A61B 5/6805* (2013.01); *A61B 5/7207* (2013.01); *A61B 5/7221* (2013.01); *A61B 5/7203* (2013.01); *A61B 2562/0219* (2013.01)

(58) Field of Classification Search
CPC ... A61B 5/7207; A61B 5/7221; A61B 5/7203; A61B 2562/0219
See application file for complete search history.

(56) References Cited

U.S. PATENT DOCUMENTS

| | | |
|---|---|---|
| 2011/0184297 A1 | 7/2011 | Vitali et al. |
| 2012/0022844 A1 | 1/2012 | Teixeira |
| 2014/0018705 A1 | 1/2014 | Wang et al. |
| 2014/0100432 A1 | 4/2014 | Golda et al. |

SYSTEM AND METHODS FOR ADAPTIVE NOISE QUANTIFICATION IN DYNAMIC BIOSIGNAL ANALYSIS

RELATED APPLICATIONS

This is a continuation application and so claims the benefit pursuant to 35 U.S.C. § 120 of a prior filed and U.S. non-provisional patent application Ser. No. 15/209,506, filed on Jul. 13, 2016, which itself claims priority pursuant to 35 U.S.C. § 119(e) to and is entitled to the filing date of U.S. provisional patent application Ser. No. 62/192,504, filed on Jul. 14, 2015, and further claims priority and is entitled to the filing date of ES application number P201531026, also filed on Jul. 14, 2015. The contents of the aforementioned applications are incorporated herein by reference.

BACKGROUND

The subject of this patent application relates generally to biosignal analysis, and more particularly to a system and associated methods for adaptive noise quantification in dynamic biosignal analysis.

Applicant(s) hereby incorporate herein by reference any and all patents and published patent applications cited or referred to in this application.

By way of background, biosignal sensors are commonly used to acquire biological signals which are used extensively in the assessment of various clinical physiological conditions—for example, without limitation, in the monitoring of a cardiac condition. Sensors are traditionally placed in contact with the skin of an individual, such as photodiode sensors (i.e., photopletismography) or voltage sensors (i.e., electrocardiography), and the physiological signals which result are examined. Some other sensors, such as magnetic sensors (i.e., magnetoencephalography) do not need to be in direct contact with the skin but rather merely in sufficient proximity to the skin. Such data may be used to monitor and/or evaluate the health and/or physical state of the wearer of such sensors.

While using such a sensor can provide an accurate measurement of a signal, there are several factors that can affect the signal quality, including, without limitation, stability, noise and/or sensibility. These limitations are due, at least in part, to factors related to relative movements between the biosignal sensor and the user which result in motion artifacts that corrupt the biosignal. This can be exacerbated when a sensor is included in a wearable device. In such a situation, the sensor needs to be integrated in a wearable—such as a garment, for example—in a minimally invasive manner that allows, for example, without limitation, flexibility and comfort to an individual's body; especially in movement. At the same time, the sensor must also be capable of measuring a signal accurately. Thus, motion artifacts are an inherent problem of biosignal sensing in the context of wearable devices and it is necessary to dispose of the proper tools to analyze the biosignal in this adverse situation. Thus, being able to estimate the signal-to-noise ratio of a biosignal is greatly important since making analysis decisions on noisy signals can lead to interpretative mistakes.

Aspects of the present invention fulfill these needs and provide further related advantages as described in the following summary.

SUMMARY

Aspects of the present invention teach certain benefits in construction and use which give rise to the exemplary advantages described below.

The present invention solves the problems described above by providing an adaptive noise quantification system and associated methods for use in the dynamic biosignal analysis. In at least one embodiment, the system includes an at least one biosignal sensor positioned and configured for obtaining data related to select vitals of the user, and transmitting said data as an at least one biosignal, and an at least one motion sensor positioned and configured for obtaining data related to a motion level of the user, and transmitting said data as an at least one motion signal. An at least one computing device is configured for receiving and processing the at least one biosignal and motion signal. A current motion stage of the user is determined based on the motion signal. A select at least one vital is extracted from suitable portions of the biosignal. A noise descriptor set formed by at least one of a morphological descriptor set and an environmental descriptor set. A noise estimator generates a noise level estimation of the biosignal based on the noise descriptor set and the motion stage of the user. A noise level of the biosignal is then calculated based on the noise level estimation of the select at least one vital.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Figure 1:
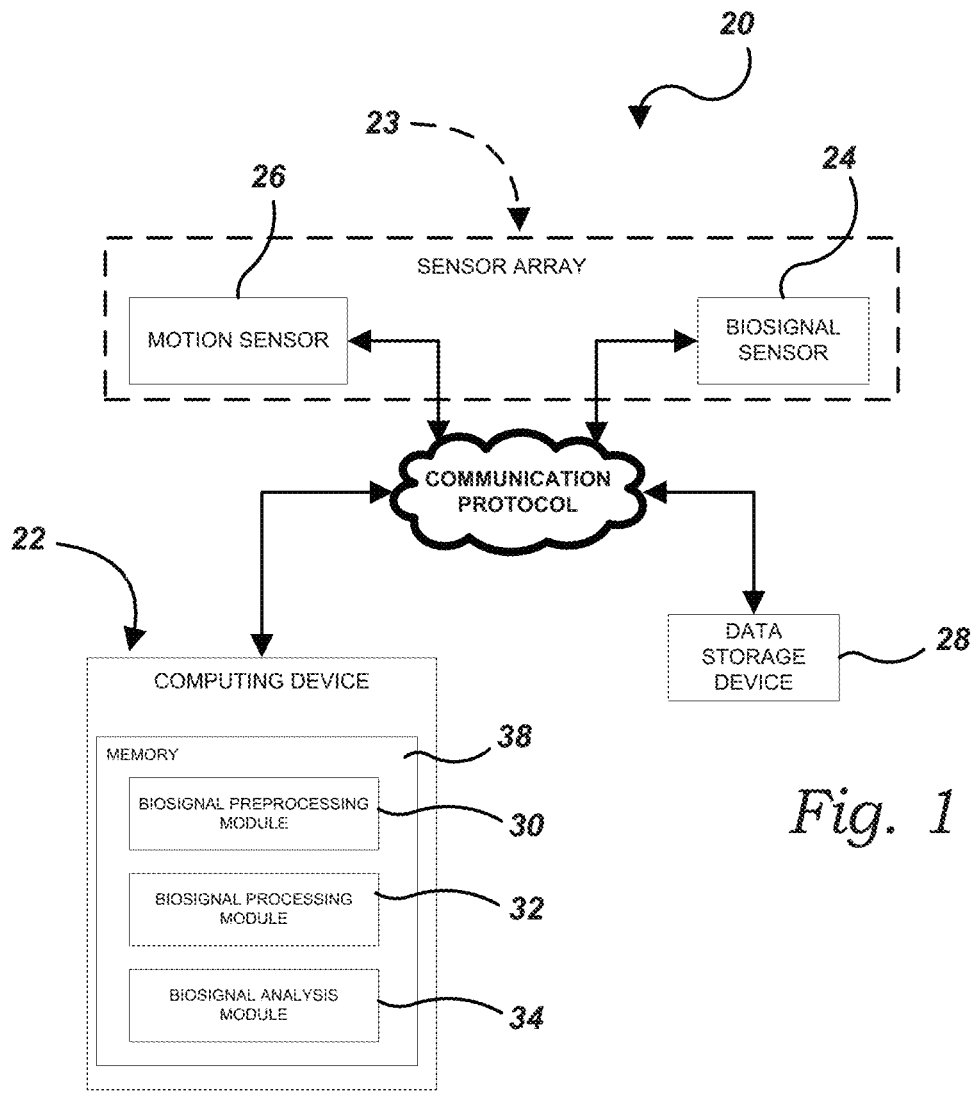
FIG. 1 is a simplified schematic view of an exemplary adaptive noise quantification system, in accordance with at least one embodiment.

Turning now to FIG. 1, there is shown a simplified schematic view of an exemplary adaptive noise quantification system 20. The system 20 provides, in at least one embodiment, an at least one computing device 22 configured for receiving and processing select data obtained by an at least one sensor array 23 comprising each of an at least one biosignal sensor 24 in communication with the computing device 22, and an at least one motion sensor 26 in communication with the computing device 22. Additionally, in at least one embodiment, an at least one data storage device 28 is in communication with the computing device 22 and configured for storing said data obtained by the at least one biosignal sensor 24 and motion sensor 26, along with certain other data as discussed further below. In at least one embodiment, the computing device 22 and data storage device 28 are one and the same unit.

At the outset, it should be noted that communication between each of the at least one computing device 22, at least one biosignal sensor 24, at least one motion sensor 26, and at least one data storage device 28 may be achieved using any wired- or wireless-based communication protocol (or combination of protocols) now known or later developed. As such, the present invention should not be read as being limited to any one particular type of communication protocol, even though certain exemplary protocols may be mentioned herein for illustrative purposes.

In at least one embodiment, the biosignal sensor 24 is positioned and configured for obtaining select data related to certain vitals of a user on which the biosignal sensor 24 is positioned. For example, in one such embodiment, the biosignal sensor 24 is an electrocardiogram ("ECG") sensor positioned and configured for obtaining data related to the user's heart activity (i.e., electrical activity of the user's heart). In still further embodiments, the at least one biosignal sensor 24 may be any other type of sensor or combination of sensors—now known or later developed—capable of obtaining data related to desired vitals of the user and which might be susceptible to unwanted noise. Thus, while the present system 20 and associated methods are herein discussed in the context of ECG sensors and the user's heart activity for illustrative purposes, the scope of the present invention should not be read as being so limited. In at least one embodiment, the motion sensor 26 is positioned and configured for obtaining select data related to the user's motion level (i.e., at rest, low level of motion, medium level of motion, high level of motion, etc.), the purpose of which is explained further below. For example, in one such embodiment, the motion sensor 26 is a microelectromechanical system ("MEMS") tri-axial accelerometer. In still further embodiments, the at least one motion sensor 26 may be any other type of sensor or combination of sensors—now known or later developed—capable of obtaining data related to the user's motion level.

With continued reference to FIG. 1, in at least one embodiment, the at least one biosignal sensor 24 is positioned on a wearable device, such as garment or other accessory being worn by the user, such as described in at least U.S. Patent Application Publication No. 2013/0338472, the contents of which are hereby incorporated herein by reference. In still further embodiments, the at least one biosignal sensor 24 may be appropriately positioned in contact with (or proximal to) the user using any other means now known or later developed. Similarly, the at least one motion sensor 26 may be appropriately positioned in contact with (or proximal to) the user using any means now known or later developed. As mentioned above, in at least one embodiment, both the at least one biosignal sensor 24 and at least one motion sensor 26 form the sensor array 23, which should be disposed in such a way that the motion data generated by the at least one motion sensor 26 reflects the motion of the at least one biosignal sensor 24. In at least one embodiment, the computing device 22 is also removably engagable with the user—either directly with the user's body or with a wearable device, such as garment or other accessory being worn by the user. In at least one such embodiment, the motion sensor 26 is positioned within the computing device 22. In at least one further such embodiment, the biosignal sensor 24 is positioned within the computing device 22. In an alternate embodiment, the computing device 22 is positioned elsewhere—either still local to the user or remotely, or even divided, with some of the functional units implemented in a computing device 22 local to the user and other units implemented in remote computer work stations.

In at least one embodiment, the computing device 22 contains the hardware and software necessary to carry out the exemplary methods for performing adaptive noise quantification in dynamic biosignal analysis as described herein. In at least one embodiment, the computing device 22 provides a biosignal preprocessing module 30, a biosignal processing module 32, and a biosignal analysis module 34, each residing in memory 38 on the computing device 22 (FIG. 1). As discussed further below, in at least one such embodiment, the biosignal preprocessing module 30 is configured for receiving a raw biosignal 40 captured by the biosignal sensor 24, discarding any portion of the biosignal 40 that is determined to be unsuitable for use, and preprocessing the suitable portions; the biosignal processing module 32 is configured for receiving the preprocessed biosignal 40 from the biosignal preprocessing module 30, extracting from the biosignal 40 the desired vitals and calculating the user's current motion level; and the biosignal analysis module 34 is configured for receiving the vitals from the biosignal processing module 32, calculating a noise descriptor set 42 for the vitals and, by using the noise descriptor set 42 and the user's current motion level, estimating a noise level 54 of the biosignal 40. It should be noted that the term "memory" is intended to include any type of electronic storage medium (or combination of storage mediums) now known or later developed, such as local hard drives, solid state drives, RAM, flash memory, secure digital ("SD") cards, external storage devices, network or cloud storage devices, integrated circuits, etc. Furthermore, the various components of the computing device 22 may reside in memory on a single computing device 22, or may separately reside on two or more computing devices 22 in communication with one another. It should also be noted that while the exemplary methods for performing adaptive noise quantification in dynamic biosignal analysis are described herein as being carried out by the above-mentioned modules 30-34, in further embodiments, the below-described functionality may be carried out by more or less modules. Thus, the present system 20 should not be read as being limited to the particular modules 30-34, and their respective functions, described herein; but rather, should be read as generally covering the methods described herein.

In use, in at least one embodiment, the system 20 utilizes a method for estimating and quantifying the amount of noise—herein referred to as the noise level 54—that is contaminating the biosignal 40 captured by the biosignal sensor 24, which takes advantage of the fact that the biosignal 40 contains some repetitive events, the vitals, which tend to be highly redundant or repetitive, while noise tends to be random. Noise is essentially random and is mainly provoked by slight and fast displacements of the biosignal sensor 24 from its position relative to the user's body. These displacements are caused by movements of the user. Furthermore, similar motion levels—and similar movements—tend to have similar noise behavior, thereby allowing the system 20 to identify and distinguish different motion stages and, in turn, make better noise estimations.

Figure 2:
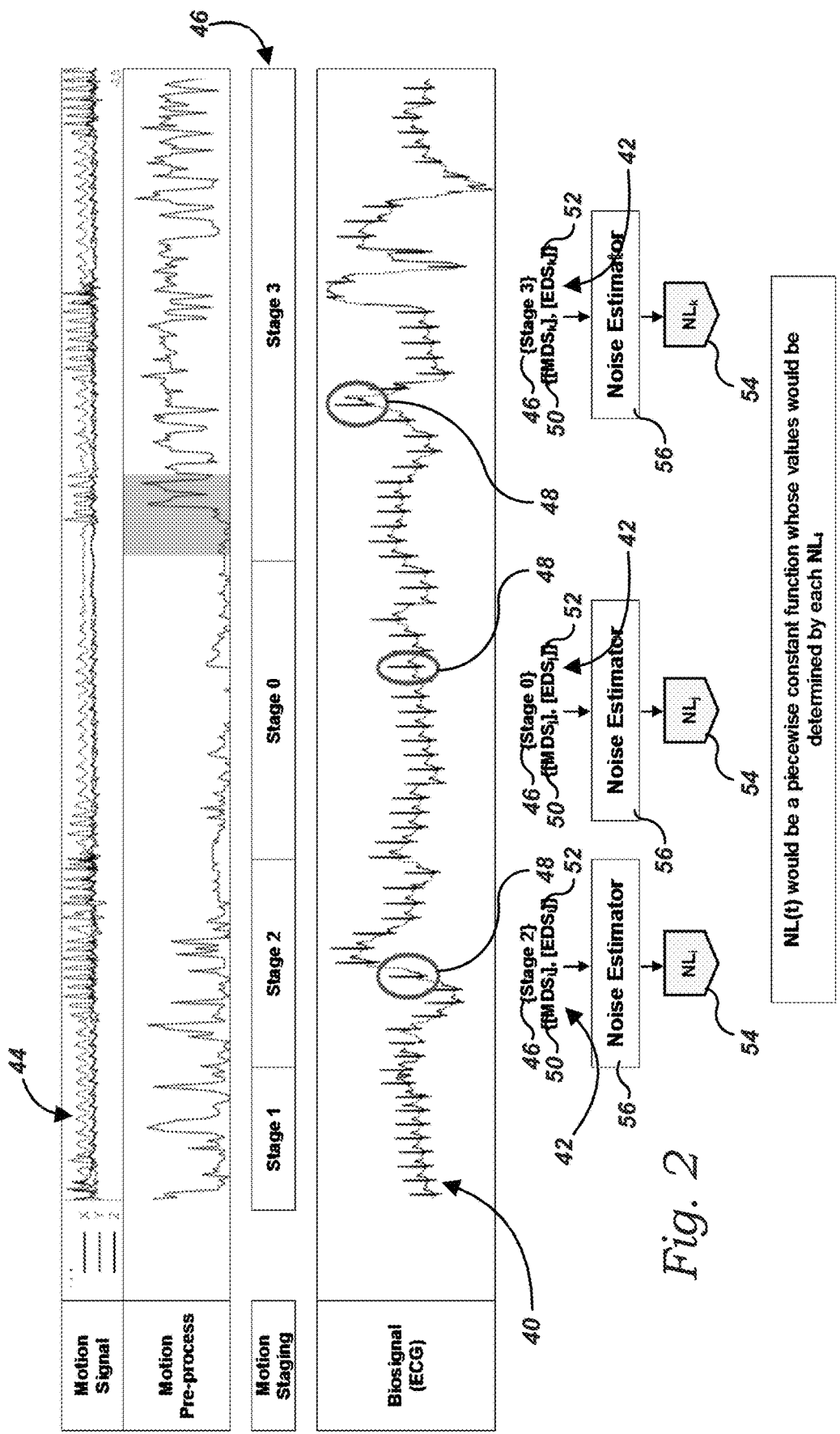
FIG. 2 is a schematic of exemplary signals captured by each of a motion sensor and biosignal sensor of the adaptive noise quantification system, in accordance with at least one embodiment.
Figure 3:
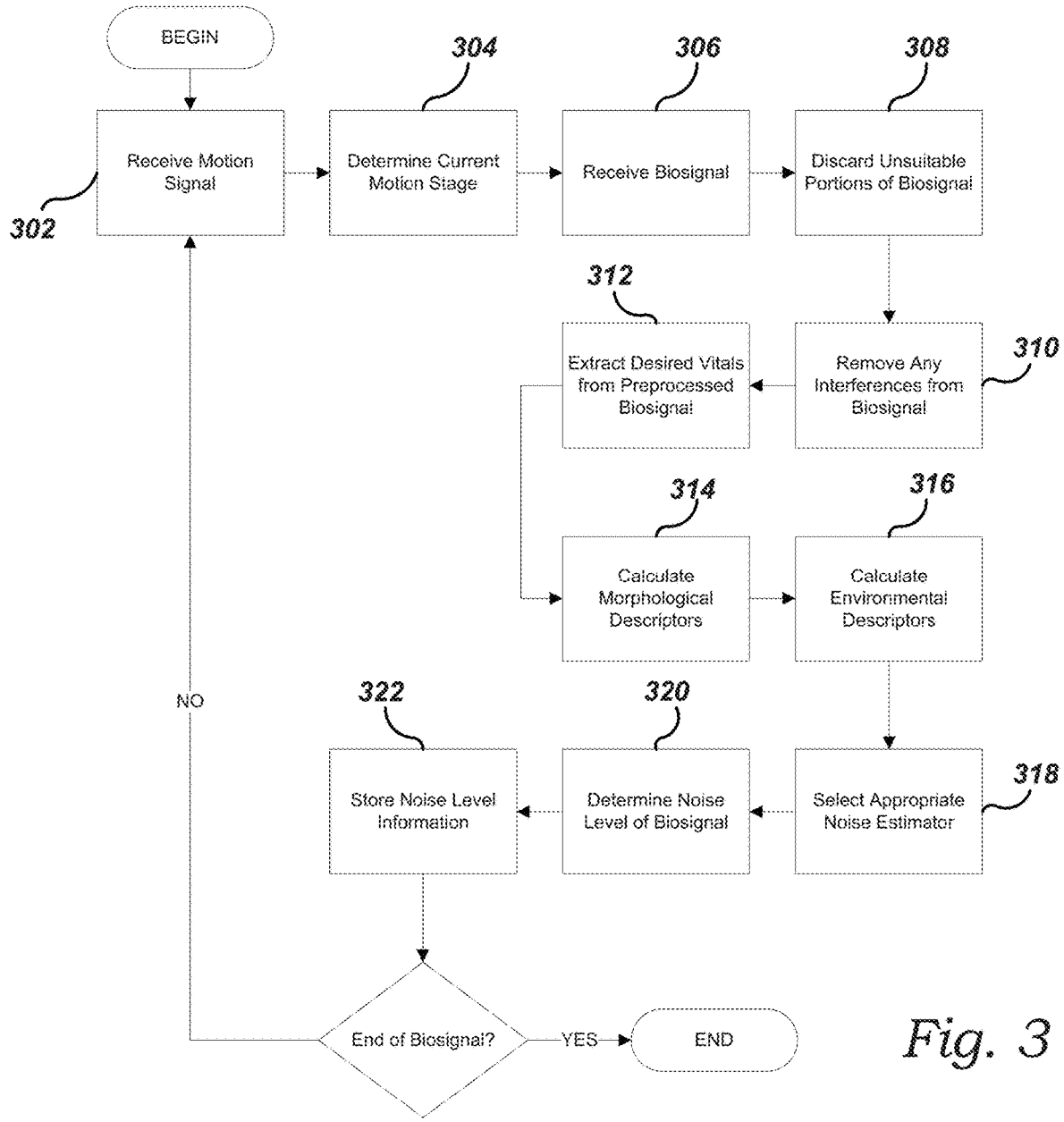
FIG. 3 is a flow diagram of an exemplary method for adaptive noise quantification in dynamic biosignal analysis, in accordance with at least one embodiment.

In at least one embodiment, as illustrated in the exemplary schematic of FIG. 2 and the flow diagram of FIG. 3, a motion signal 44 is captured by the motion sensor 26 and transmitted to the computing device 22 (302), where it is analyzed to determine a current motion stage 46 of the user (304)—i.e., the wearer of at least the motion sensor 26 and biosignal sensor 24. As mentioned above, in at least one embodiment, the motion sensor 26 is positioned and configured for obtaining select data related to the user's motion level (i.e., at rest, low level of motion, medium level of motion, high level of motion, etc.). Thus, in at least one embodiment, the motion stage 46 of the user is comprised of at least the user's motion level. In at least one embodiment, the computing device 22 extracts the necessary portions of the motion signal 44 and passes them to a classification function that determines the motion stage 46. In at least one such embodiment, where the motion sensor 26 is a MEMS tri-axial accelerometer, the motion sensor 26 measures accelerations in each of an orthogonal X, Y and Z direction and transmits the data, via the communication protocol, to the computing device 22. Using that data, the computing device 22 is able to calculate various parameters, including but not limited to a motion index ("MI") or a median absolute deviation ("MAD"). In a bit more detail, in at least one embodiment, the motion index is a 1-second window integration of the modulus of the X, Y, Z vector without gravitational influence (i.e., a high pass filtering of accelerometry components) using the following formula:

$$MI = \frac{\sum_{i=1}^{n} |\overrightarrow{ACC}|}{n}, |\overrightarrow{ACC}| = \sqrt{ACC_x^2 + ACC_y^2 + ACC_z^2}$$

Relatedly, in at least one embodiment, the mean absolute deviation is derived using the following formula:

$$MAD = \frac{\sum_{i=1}^{n} \left| |\overrightarrow{ACC}|_i - \overline{|\overrightarrow{ACC}|} \right|}{n}, \overline{|\overrightarrow{ACC}|} = \text{modulus average value}$$

Thus, in at least one embodiment, the classification function used to determine the motion stage 46 is a threshold function dependent on previous parameters calculated in predefined intervals of time.

With continued reference to FIG. 3, in at least one embodiment, the biosignal 40 is captured by the biosignal sensor 24 and is also transmitted to the computing device 22 (306), where it is analyzed to determine and obtain the relevant vitals of the user. In at least one such embodiment, where the biosignal sensor 24 is an ECG sensor or the like, the biosignal sensor 24 senses and transmits raw ECG data, via the communication protocol, to the computing device 22. As mentioned above, in at least one embodiment, the biosignal 40 is first received by the biosignal preprocessing module 30, where any portion of the biosignal 40 determined to be unsuitable for use (i.e., saturated, etc.) is discarded (308). Additionally, any remaining portions of the biosignal 40 are improved by filtering any baseline, power line or high frequency interferences (310).

The biosignal processing module 32 then extracts from the preprocessed biosignal 40 the desired vitals (312). In at least one embodiment, where the biosignal sensor 24 is an ECG sensor or the like, the vitals are the heart beats that the biosignal processing module 32 is configured to detect.

The biosignal analysis module 34 then calculates a noise descriptor set 42 for each vital extracted by the biosignal processing module 32. In at least one embodiment, where the biosignal sensor 24 is an ECG sensor or the like, the biosignal analysis module 34 obtains the noise descriptor set 42 for each heart beat, which will be used, together with the corresponding motion stage 46, to estimate the noise level 54 of the beat. In a bit more detail, in at least one embodiment, each noise descriptor set 42 is comprised of at least one of one a morphological descriptor set ("MDS") 50, which describes the vitals, and an environmental descriptor set ("EDS") 52, which describes the environment context of the vitals. In at least one such embodiment, the biosignal analysis module 34 calculates three parameters related to the morphological descriptor set 50 (314): a maximum second derivative ("Max2Der"), a derivative zero crosses ("DerivZX"), and a derivative asymmetry ("DerivAsym"). The Max2Der parameter is the maximum value of the absolute second derivative. As the second derivative describes the variation of the slope of the biosignal 40, the maximum absolute value characterizes the concavity/convexity of the biosignal 40; thus, high values indicate sharp peaks, such as spikes. The DerivZX parameter is the zero crosses count of the first derivative, modified by nullifying all values with an absolute value lower than ten percent (10%) of the maximum absolute value. This parameter is high when the biosignal 40 has too many oscillations, such as when the biosignal 40 is very noisy. The DerivAsym parameter is the ratio between the integral of the second half of the absolute derivative and the integral of the first half. In at least one embodiment, for each noise descriptor set 42, the biosignal analysis module 34 also calculates the environmental descriptor set 52 (316), to be used by the computing device 22. For example, one such parameter of the environmental descriptor set 52 is related to adjacent heart beat segments in the biosignal 40—when a given heart beat is adjacent to or near a relatively noisy segment in the biosignal 40, such is typically indicative of a transition from a very noisy portion of the biosignal 40 to a relatively clean portion of the biosignal 40. Another exemplary parameter of the environmental descriptor set 52 is related to the amplitude of a given heart beat—relatively lower amplitudes tend to be more suitable to having a low signal-to-noise ratio. Another exemplary parameter of the environmental descriptor set 52 is the similarity of the vital to the neighbor vitals, since noisy vitals are less similar to its neighbors and non-noisy vitals should be almost identical. Thus, in at least one embodiment, the noise descriptor set 42 is constructed by grouping both the morphological descriptor set 50 and environmental descriptor set 52 (i.e., {[MDS], [EDS]}.

With continued reference to FIGS. 2 and 3, in at least one embodiment, with the motion stage 46 of the user determined (304), the computing system 22 uses an appropriate noise estimator 56 (318) to determine the noise level 54 of the biosignal 40 (320) using as input information the noise descriptor set 42 and the motion stage 46. In a bit more detail, in at least one such embodiment, the system 20 provides a plurality of noise estimators 56 with each being tailored and trained to model a different noise behavior for a particular motion stage 46; so each noise estimator 56 is specialized in estimating the noise level 54 of a particular motion stage 46. Additionally, the noise estimator 56 is preferably an at least one artificially intelligent system—such as a neural network, in at least one embodiment—capable of estimating the noise level 54 based on the morphological descriptor set 50 and environmental descriptor set 52 associated with a given noise descriptor set 42 of the biosignal 40. The output of the noise estimator 56 is a noise level 54 estimation ("NL") for the biosignal 40, and a time-dependent noise level 54 function can be obtained for the biosignal 40. This function has a constant value calculated for each discrete unit of the vitals (such as a heart beat, where the biosignal sensor 24 is an ECG sensor or the like), so it is a time-dependent piecewise constant function. In at least one such embodiment, the function is defined as:

$$NL(t)=NL_{vital_i} \forall t \in [\text{Start}_{vital_i}, \text{Start}_{vital_{i+1}}]$$

In at least one embodiment, once the noise level 54 for the biosignal 40 has been obtained, this information is stored (322) so that it can be used in different ways by subsequent processing algorithms, such as heart rate calculation methods or arrhythmia detection for example. Thus, the system 20 is capable of performing noise quantification methods on biosignals by analyzing the motion data associated with the user and dynamically adapting the biosignal assessment based on that motion, independently of the physical activity which is being performed by the user.

Aspects of the present specification may also be described as follows:

1. A method for adaptive noise quantification in dynamic biosignal analysis of a user, the method comprising the steps of: transmitting to a computing device an at least one motion signal captured by an at least one motion sensor, the motion signal containing data related to a motion level of the user; transmitting to the computing device an at least one biosignal captured by an at least one biosignal sensor, the biosignal containing data related to a select at least one vital of the user; determining a motion stage of the user based on the at least one motion signal; discarding any portion of the biosignal determined to be unsuitable for use; extracting the select at least one vital from the remaining portions of the biosignal; calculating, for each select at least one vital, a noise descriptor set comprising at least one of a morphological descriptor set and an environmental descriptor set; generating a noise level estimation of the select at least one vital based on at least one of the noise descriptor set and the motion stage of the user; and calculating a noise level of the biosignal based on the noise level estimation of the select at least one vital.

2. The method according to embodiment 1, further comprising the step of positioning the at least one motion sensor on a wearable device worn by the user.

3. The method according to embodiments 1-2, wherein the step of positioning the at least one motion sensor further comprises the step of positioning an at least one tri-axial accelerometer on the wearable device worn by the user.

4. The method according to embodiments 1-3, further comprising the step of positioning the at least one biosignal sensor on a wearable device worn by the user.

5. The method according to embodiments 1-4, wherein the step of positioning the at least one biosignal sensor further comprises the step of positioning an at least one electrocardiogram sensor on the wearable device worn by the user.

6. The method according to embodiments 1-5, further comprising the step of grouping the at least one motion signal based on motion stages, thereby allowing the computing device to more accurately estimate, identify and separate out noise while performing dynamic biosignal analysis.

7. The method according to embodiments 1-6, further comprising the step of removing any baseline, power line, and high frequency interferences in the remaining portions of the biosignal.

8. The method according to embodiments 1-7, further comprising the step of selecting an appropriate noise estimator, based on the motion stage of the user, for generating the noise level estimation of the biosignal.

9. A method for adaptive noise quantification in dynamic biosignal analysis of a user, the method comprising the steps of: implementing each of a biosignal preprocessing module, a biosignal processing module, and a biosignal analysis module in memory on a computing device; transmitting to the computing device an at least one motion signal captured by an at least one motion sensor, the motion signal containing data related to a motion level of the user; transmitting to the computing device an at least one biosignal captured by an at least one biosignal sensor, the biosignal containing data related to a select at least one vital of the user; the biosignal preprocessing module discarding any portion of the biosignal determined to be unsuitable for use; the biosignal processing module extracting the select at least one vital from the remaining portions of the biosignal; the biosignal processing module determining a motion stage of the user based on the at least one motion signal; the biosignal analysis module calculating a noise descriptor set comprising at least of one of a morphological descriptor set and an environmental descriptor set; the biosignal analysis module generating a noise level estimation of the select at least one vital based on the noise descriptor set and the motion stage of the user; and the biosignal analysis module calculating a noise level of the biosignal based on the noise level estimation of the select at least one vital.

10. The method according to embodiment 9, further comprising the step of the biosignal preprocessing module removing any baseline, power line, and high frequency interferences in the remaining portions of the biosignal.

11. The method according to embodiments 9-10, further comprising the step of the biosignal analysis module selecting an appropriate noise estimator, based on the motion stage of the user, for generating the noise level estimation of the biosignal.

12. An adaptive noise quantification system for use in dynamic biosignal analysis of a user, the system comprising: an at least one biosignal sensor positioned and configured for obtaining data related to a select at least one vital of the user, and transmitting said data as an at least one biosignal; an at least one motion sensor positioned and configured for obtaining data related to an motion level of the user, and transmitting said data as an at least one motion signal; an at least one computing device configured for receiving and processing the at least one biosignal and motion signal; a biosignal preprocessing module residing in memory on the computing device and configured for discarding any portion of the biosignal determined to be unsuitable for use; a biosignal processing module residing in memory on the computing device and configured for extracting the select at least one vital from the remaining portions of the biosignal, and determining a current motion stage of the user based on the at least one motion signal; and a biosignal analysis module residing in memory on the computing device and configured for calculating a noise descriptor set, comprising at least one of a morphological descriptor set and an environmental descriptor set.

13. The adaptive noise quantification system according to embodiment 12, wherein the at least one biosignal sensor is an electrocardiogram sensor positioned and configured for obtaining data related to a heart activity of the user.

14. The adaptive noise quantification system according to embodiments 12-13, wherein the at least one motion sensor is a tri-axial accelerometer.

15. The adaptive noise quantification system according to embodiments 12-14, wherein the at least one biosignal sensor is positioned on a wearable device worn by the user.

16. The adaptive noise quantification system according to embodiments 12-15, wherein the at least one motion sensor is positioned on a wearable device worn by the user.

17. The adaptive noise quantification system according to embodiments 12-16, wherein the at least one biosignal sensor and at least one motion sensor are integrated in an at least one sensor array.

In closing, regarding the exemplary embodiments of the present invention as shown and described herein, it will be appreciated that a system and associated methods for adaptive noise quantification in dynamic biosignal analysis is disclosed. Because the principles of the invention may be practiced in a number of configurations beyond those shown and described, it is to be understood that the invention is not in any way limited by the exemplary embodiments, but is generally directed to a system and associated methods for adaptive noise quantification in dynamic biosignal analysis and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention. Furthermore, the various features of each of the above-described embodiments may be combined in any logical manner and are intended to be included within the scope of the present invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

Any claims intended to be treated under 35 U.S.C. § 112(f) will begin with the words "means for," but use of the term "for" in any other context is not intended to invoke treatment under 35 U.S.C. § 112(f). Accordingly, Applicant reserves the right to pursue additional claims after filing this application, in either this application or in a continuing application.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment. Additionally, the various illustrative logical blocks, modules, methods, and algorithm processes and sequences described in connection with the embodiments disclosed herein can be implemented as electronic hardware, computer software, or combinations of both. To clearly illustrate this interchangeability of hardware and software, various illustrative components, blocks, modules, and process actions have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of this document.

The phrase "non-transitory," in addition to having its ordinary meaning, as used in this document means "enduring or long-lived". The phrase "non-transitory computer readable medium," in addition to having its ordinary meaning, includes any and all computer readable mediums, with the sole exception of a transitory, propagating signal. This includes, by way of example and not limitation, non-transitory computer-readable mediums such as register memory, processor cache and random-access memory ("RAM").

The methods as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multi-chip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A method for adaptive noise quantification in dynamic biosignal analysis of a user, the method comprising:
    positioning each of an at least one motion sensor and an at least one biosignal sensor on a wearable device worn by the user;
    capturing, via the at least one motion sensor, an at least one motion signal containing data related to a motion level of the user, including accelerations in each of an orthogonal X direction ("ACCx"), Y direction ("ACCy") and Z direction ("ACCz");
    the at least one motion sensor transmitting the at least one motion signal to a computing device;

capturing, via the at least one biosignal sensor, an at least one biosignal containing data related to a select at least one vital of the user;
the at least one biosignal sensor transmitting the at least one biosignal to the computing device;
the computing device calculating at least one of a motion index ("MI") and a median absolute deviation ("MAD") based on the at least one motion signal, wherein the motion index is calculated using the formula $$MI = \frac{\sum_{i=1}^{n} |\overrightarrow{ACC}|}{n}, |\overrightarrow{ACC}| = \sqrt{ACC_x^2 + ACC_y^2 + ACC_z^2},$$

and wherein the median absolute deviation is calculated using the formula $$MAD = \frac{\sum_{i=1}^{n} \left||\overrightarrow{ACC}|_i - \overline{|\overrightarrow{ACC}|}\right|}{n}, \overline{|\overrightarrow{ACC}|} = \text{modulus average value};$$

the computing device determining a motion stage of the user based on at least one of the motion index and median absolute deviation;
the computing device extracting the select at least one vital from the biosignal;
the computing device calculating, for each select at least one vital, a noise descriptor set comprising at least one of a morphological descriptor set and an environmental descriptor set;
the computing device generating a noise level estimation of the select at least one vital based on at least one of the noise descriptor set and the motion stage of the user; and
the computing device calculating a noise level of the biosignal based on the noise level estimation of the select at least one vital.

2. The method of claim 1, wherein positioning the at least one motion sensor further comprises positioning an at least one tri-axial accelerometer on the wearable device worn by the user.

3. The method of claim 1, wherein positioning the at least one biosignal sensor further comprises positioning an at least one electrocardiogram sensor on the wearable device worn by the user.

4. The method of claim 1, further comprising the computing device grouping the at least one motion signal based on motion stages, thereby allowing the computing device to further estimate, identify and separate out noise while performing dynamic biosignal analysis.

5. The method of claim 1, further comprising the computing device removing any baseline, power line, and high frequency interferences in the biosignal.

6. The method of claim 1, further comprising the computing device selecting a noise estimator, based on the motion stage of the user, for generating the noise level estimation of the biosignal.

7. A method for adaptive noise quantification in dynamic biosignal analysis of a user, the method comprising:
implementing each of a biosignal processing module and a biosignal analysis module in memory on a computing device;
positioning each of an at least one motion sensor and an at least one biosignal sensor on a wearable device worn by the user;
capturing, via the at least one motion sensor, an at least one motion signal containing data related to a motion level of the user, including accelerations in each of an orthogonal X direction ("ACCx"), Y direction ("ACCy") and Z direction ("ACCz");
the at least one motion sensor transmitting the at least one motion signal to a computing device;
capturing, via the at least one biosignal sensor, an at least one biosignal containing data related to a select at least one vital of the user;
the at least one biosignal sensor transmitting the at least one biosignal to the computing device;
the biosignal processing module extracting the select at least one vital from the biosignal;
the biosignal processing module calculating at least one of a motion index ("MI") and a median absolute deviation ("MAD") based on the at least one motion signal, wherein the motion index is calculated using the formula $$MI = \frac{\sum_{i=1}^{n} |\overrightarrow{ACC}|}{n}, |\overrightarrow{ACC}| = \sqrt{ACC_x^2 + ACC_y^2 + ACC_z^2},$$

and wherein the median absolute deviation is calculated using the formula $$MAD = \frac{\sum_{i=1}^{n} \left||\overrightarrow{ACC}|_i - \overline{|\overrightarrow{ACC}|}\right|}{n}, \overline{|\overrightarrow{ACC}|} = \text{modulus average value},$$

the biosignal processing module determining a motion stage of the user based on at least one of the motion index and median absolute deviation;
the biosignal analysis module calculating a noise descriptor set comprising at least of one of a morphological descriptor set and an environmental descriptor set;
the biosignal analysis module generating a noise level estimation of the select at least one vital based on the noise descriptor set and the motion stage of the user; and
the biosignal analysis module calculating a noise level of the biosignal based on the noise level estimation of the select at least one vital.

8. The method of claim 7, further comprising:
implementing a biosignal preprocessing module in memory on a computing device; and
the biosignal preprocessing module removing any baseline, power line, and high frequency interferences in the biosignal.

9. The method of claim 7, further comprising the biosignal analysis module selecting a noise estimator, based on the motion stage of the user, for generating the noise level estimation of the biosignal.

10. An adaptive noise quantification system for use in dynamic biosignal analysis of a user, the system comprising:
an at least one biosignal sensor positioned on a wearable device worn by the user and configured for obtaining data related to a select at least one vital of the user, and transmitting said data as an at least one biosignal;

an at least one motion sensor positioned on the wearable device and configured for obtaining data related to an motion level of the user, and transmitting said data as an at least one motion signal, said data including accelerations in each of an orthogonal X direction ("ACCx"), Y direction ("ACCy") and Z direction ("ACCz");

an at least one computing device configured for receiving and processing the at least one biosignal and motion signal;

a biosignal processing module residing in memory on the computing device and configured for extracting the select at least one vital from the biosignal, calculating at least one of a motion index ("MI") and a median absolute deviation ("MAD") based on the at least one motion signal, wherein the motion index is calculated using the formula $$MI = \frac{\sum_{i=1}^{n}|\overrightarrow{ACC}|}{n}, |\overrightarrow{ACC}| = \sqrt{ACC_x^2 + ACC_y^2 + ACC_z^2},$$

and wherein the median absolute deviation is calculated using the formula $$MAD = \frac{\sum_{i=1}^{n}\left||\overrightarrow{ACC}|_i - \overline{|\overrightarrow{ACC}|}\right|}{n}, \overline{|\overrightarrow{ACC}|} = \text{modulus average value},$$

and determining a current motion stage of the user based on at least one of the motion index and median absolute deviation; and a biosignal analysis module residing in memory on the computing device and configured for calculating a noise descriptor set, comprising at least one of a morphological descriptor set and an environmental descriptor set.

11. The adaptive noise quantification system of claim 10, wherein the at least one biosignal sensor is an electrocardiogram sensor positioned and configured for obtaining data related to a heart activity of the user.

12. The adaptive noise quantification system of claim 10, wherein the at least one motion sensor is a tri-axial accelerometer.

13. The adaptive noise quantification system of claim 10, wherein the at least one biosignal sensor and at least one motion sensor are integrated in an at least one sensor array.

14. The adaptive noise quantification system of claim 10, further comprising a biosignal preprocessing module residing in memory on the computing device and configured for discarding select portions of the biosignal.

* * * * *